US012465693B1

(12) United States Patent
Stankus et al.

(10) Patent No.: US 12,465,693 B1
(45) Date of Patent: Nov. 11, 2025

(54) DOSING DELIVERY DEVICES, SYSTEMS, AND METHODS

(71) Applicant: Resurge Therapeutics, Inc., San Jose, CA (US)

(72) Inventors: John J. Stankus, San Jose, CA (US); Benjamyn Serna, San Jose, CA (US); Olof Mikael Trollsas, San Jose, CA (US)

(73) Assignee: Resurge Therapeutics, Inc., San Jose, CA (US)

( * ) Notice: Subject to any disclaimer, the term of this patent is extended or adjusted under 35 U.S.C. 154(b) by 0 days.

(21) Appl. No.: 19/012,613

(22) Filed: Jan. 7, 2025

(51) Int. Cl.
*A61M 5/315* (2006.01)

(52) U.S. Cl.
CPC ................................ *A61M 5/31528* (2013.01)

(58) Field of Classification Search
CPC ...... A61M 2005/3139; A61M 5/31581; A61M 5/31583; A61M 5/31586
See application file for complete search history.

(56) References Cited

U.S. PATENT DOCUMENTS

| | | | | |
|---|---|---|---|---|
| 2,457,977 | A * | 1/1949 | Cookson | A61M 5/1456 128/DIG. 1 |
| 2,722,931 | A * | 11/1955 | May | A61M 5/30 604/68 |
| 2,764,980 | A * | 10/1956 | Ralph | A61M 5/1452 604/154 |
| 3,161,323 | A | 12/1964 | Bent | |
| 3,395,704 | A * | 8/1968 | Frey | A61M 5/24 200/332.2 |
| 4,415,101 | A | 11/1983 | Shapiro et al. | |
| 5,034,004 | A * | 7/1991 | Crankshaw | A61M 5/1456 D24/111 |
| 7,922,699 | B2 | 4/2011 | Baba et al. | |
| 8,123,084 | B2 | 2/2012 | Reynolds et al. | |
| 8,998,880 | B2 | 4/2015 | Reynolds et al. | |
| 9,114,216 | B2 | 8/2015 | Sutkin et al. | |
| 9,186,464 | B2 | 11/2015 | Franklin | |
| 9,724,479 | B2 | 8/2017 | Sutkin et al. | |
| 9,814,831 | B2 | 11/2017 | Gonnelli | |
| 9,950,855 | B1 | 4/2018 | Holland et al. | |
| 10,220,152 | B2 | 3/2019 | Cammish et al. | |
| 10,265,477 | B2 | 4/2019 | Schwab et al. | |
| 10,307,544 | B2 | 6/2019 | Jones et al. | |
| 10,342,928 | B2 | 7/2019 | Spenser et al. | |
| 10,391,253 | B1 | 8/2019 | Joseph et al. | |

(Continued)

*Primary Examiner* — James D Ponton
*Assistant Examiner* — Hong-Van N Trinh
(74) *Attorney, Agent, or Firm* — CASIMIR JONES, S.C.; Brian F. Bradley

(57) ABSTRACT

A method for treating a prostate comprising the steps of using a needle-syringe coupled to a dose delivery device. The dose delivery device comprises a housing, a holder configured to receive a first portion of the needle-syringe, and an arm at least partially extending from the housing. The arm includes a surface configured to engage a second portion of the needle-syringe. The dose delivery device further includes an actuation member movable with respect to the housing, a worm coupled to the actuation member, a worm gear engaged with the worm, and a pinion gear fixed to the worm gear and engaged with the arm. The arm moves along a translation axis in response to user actuation of the actuation member about a rotational axis.

18 Claims, 6 Drawing Sheets

(56) References Cited

U.S. PATENT DOCUMENTS

| | | | | |
|---|---|---|---|---|
| 11,110,227 | B2 | 9/2021 | Muise et al. | |
| 11,291,774 | B2 | 4/2022 | Bayer et al. | |
| 11,534,549 | B2 | 12/2022 | Carrel et al. | |
| 11,684,719 | B2 | 6/2023 | Franklin et al. | |
| 11,911,600 | B2 | 2/2024 | Carrel | |
| 2008/0255525 | A1 | 10/2008 | Taufig | |
| 2010/0137802 | A1* | 6/2010 | Yodfat | A61M 5/14248 604/152 |
| 2012/0016303 | A1* | 1/2012 | Ohta | A61M 5/14546 604/131 |
| 2012/0259289 | A1 | 10/2012 | Byrnes et al. | |
| 2013/0296778 | A1 | 11/2013 | Damgaard-Soerensen et al. | |
| 2014/0088553 | A1 | 3/2014 | Hetherington | |
| 2014/0236087 | A1* | 8/2014 | Alderete, Jr. | A61M 5/14566 604/152 |
| 2015/0182702 | A1 | 7/2015 | Sutkin et al. | |
| 2016/0158453 | A1 | 6/2016 | Oakley et al. | |
| 2017/0296753 | A1 | 10/2017 | Rowe et al. | |
| 2020/0086055 | A1* | 3/2020 | Verlaak | A61M 5/1452 |
| 2020/0197924 | A1 | 6/2020 | Anitua Aldecoa | |
| 2021/0205541 | A1 | 7/2021 | King et al. | |
| 2021/0338936 | A1 | 11/2021 | Pedersen et al. | |
| 2023/0112837 | A1* | 4/2023 | Arthur, III | A61M 5/14546 604/155 |
| 2023/0248688 | A1 | 8/2023 | Trollsas et al. | |

* cited by examiner

DOSING DELIVERY DEVICES, SYSTEMS, AND METHODS

TECHNICAL FIELD

Minimally invasive, local treatments for men's health and, more particularly, lower urinary tract symptoms, including benign prostatic hyperplasia.

BACKGROUND

Enlarged prostate or benign prostatic hyperplasia (BPH) negatively affects the quality of life in 60% of men over the age of 60 and 90% of men over the age of 70. BPH currently impacts more than 14 million men in the United States and about 94 million men globally. In the U.S. alone, BPH represents a $20 billion market opportunity. The symptoms of this growing healthcare challenge include urinary storage and voiding issues including retention. When left untreated BPH can lead to sexual dysfunction, bladder and kidney damage, and ultimately death. Beyond the significant negative impact on quality of life, BPH is one of the costliest and most frequent treatment segments of urology. Current treatments, such as oral drugs, however, have limited efficacy, require long term compliance, and cause significant side effects. Surgery and other procedures are invasive and also have risks of significant side effects.

Another common type of prostate treatment is treatment for cancerous or pre-cancerous conditions (e.g., non-malignant tumors). The volume of drug (on a per-volume of prostate basis) is different when treating a tumor or cancer than when treating BPH.

For both prostate treatments, delivery of small doses of a viscous composition deep into the body is challenging. These challenges of delivering small doses (referred to herein as "unit volumes") are discussed in U.S. Pat. No. 12,090,136, incorporated herein by reference. For example, small unit volumes are required to be delivered with high volumetric and spatial accuracy and precision to achieve a reduction in prostate size for treatment of BPH without adverse consequences. A health professional needs to deliver the unit doses along a needle track without the need to look at the needle or the syringe.

Conventional small volume needle-syringes have 50 microliter graduations, which the user must carefully view when dispensing doses of the unit volume. The challenges of delivering this unit volume included accuracy as well as overcoming the backpressure. One challenge faced was the tendency for the syringe plunger to reverse because of the fluid pressure. To achieve the desired volume the plunger stroke would need to exceed the labeled volume to account for the back pressure. As such the smallest unit volume was limited.

SUMMARY

In some aspects, the presently disclosed subject matter provides a device comprising a housing, a holder configured to receive a first portion of a needle-syringe, and an arm at least partially extending from the housing. The arm includes a surface configured to engage a second portion of the needle-syringe. The device further comprises an actuation member movable with respect to the housing, a worm coupled to the actuation member, a worm gear engaged with the worm, and a pinion gear fixed to the worm gear and engaged with a gear rack the arm. The arm moves along a translation axis in response to user actuation of the actuation member about a rotational axis.

In other aspects, the presently disclosed subject matter provides an apparatus comprising a needle-syringe with a first portion, a second portion, and a plurality of unit volumes of a composition comprising a drug, polymer and solvent. The apparatus further comprises a dose delivery device with a housing, a holder configured to receive the first portion of the needle-syringe, and an arm at least partially extending from the housing. The arm includes a surface configured to engage the second portion of the needle-syringe. The dose delivery device further includes an actuation member movable with respect to the housing, a one-way transmission coupled between the actuation member and the arm, wherein the arm moves along a translation axis in response to user actuation of the actuation member about a rotational axis. The needle-syringe dispenses one of the plurality of unit volumes with a volumetric accuracy of at least 90% in response to the actuation member rotating more than 90 degrees about the rotational axis.

In yet other aspects, the presently disclosed subject matter provides a method for treating a prostate comprising the steps of: using a needle-syringe coupled to a dose delivery device, the dose delivery device having a user actuation portion, a one-way transmission, and an arm; wherein the arm is configured to engage a plunger of the needle-syringe to dispense no more than a unit volume from the needle; and rotating the user actuation portion more than 90 degrees to cause the arm to displace the plunger, thereby dispensing the unit volume from the needle; wherein no more than a unit volume is dispensed from the needle in respond to rotating the user actuation portion more than 90 degrees.

In yet other aspects, the presently disclosed subject matter provides an apparatus, comprising: a needle-syringe containing an SRF, and a dose delivery device, comprising: a housing; a holder configured to receive a first portion of the needle-syringe; an arm at least partially extending from the housing; wherein the arm engages a second portion of the needle-syringe; an actuation member movable with respect to the housing; a worm coupled to the actuation member; a worm gear engaged with the worm; and a pinion gear fixed to the worm gear and engaged with the arm; wherein the arm moves along a translation axis in response to user actuation of the actuation member about a rotational axis.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1A:
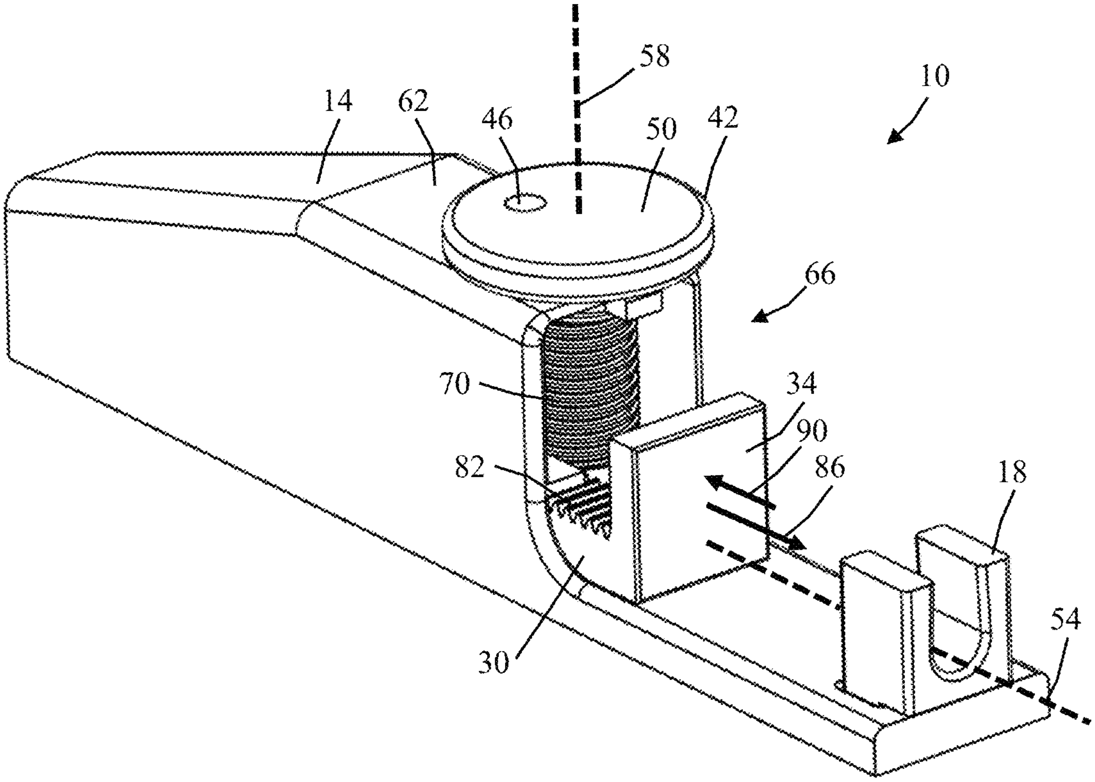

Having thus described the presently disclosed subject matter in general terms, reference will now be made to the accompanying drawings, which are not necessarily drawn to scale, and wherein:

FIG. 1A is a perspective view of a dose delivery device in a first configuration.

Figure 1B:
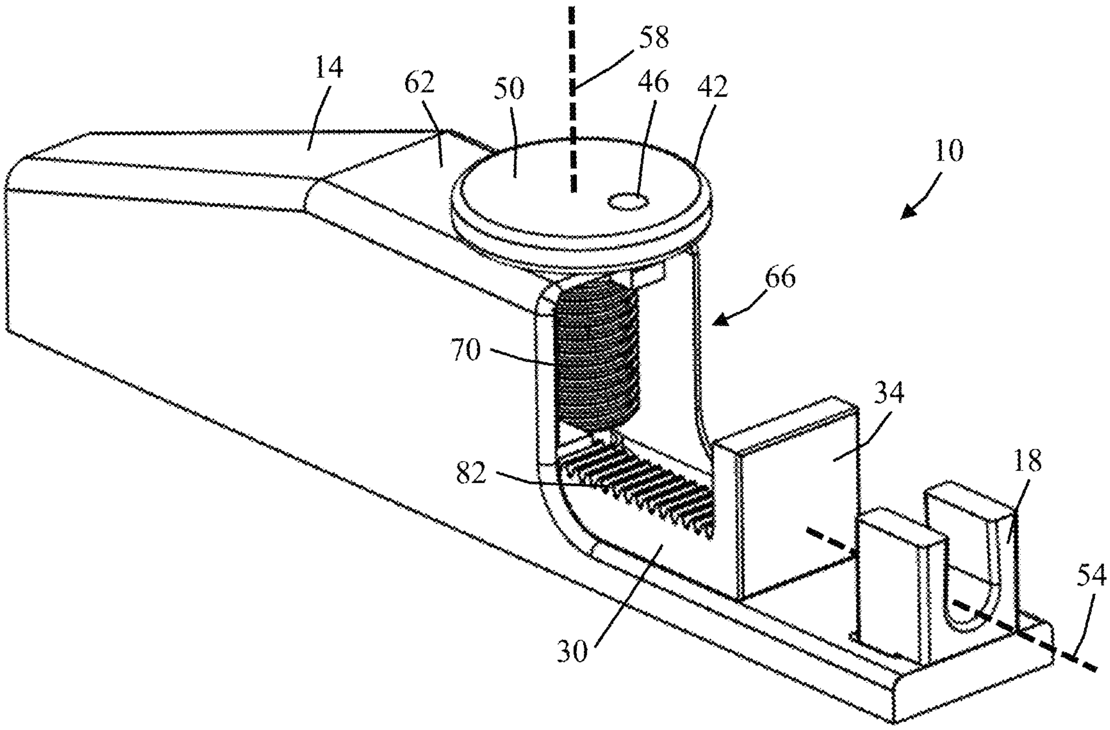

FIG. 1B is a perspective view of the dose delivery device of FIG. 1A in a second configuration.

Figure 2:
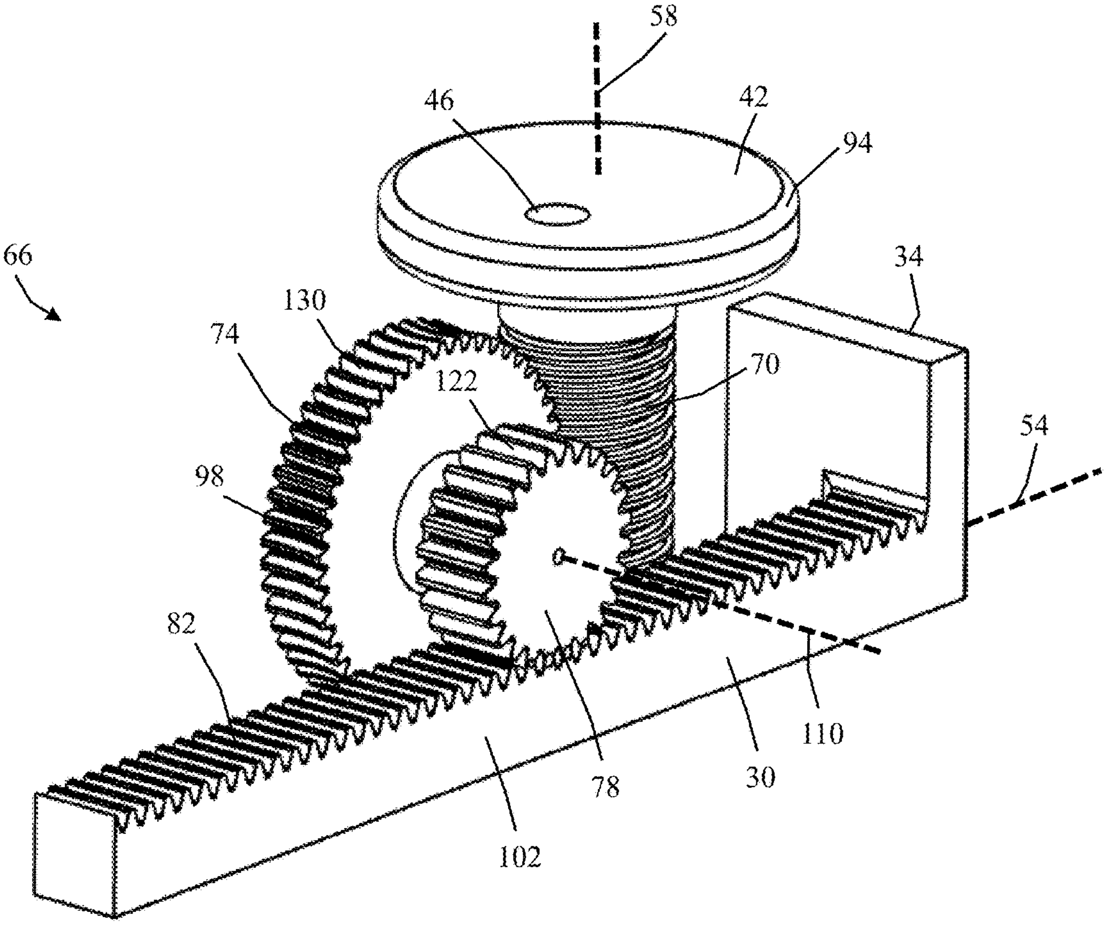

FIG. 2 is a perspective view of a transmission of the dose delivery device of FIG. 1A.

Figure 3:
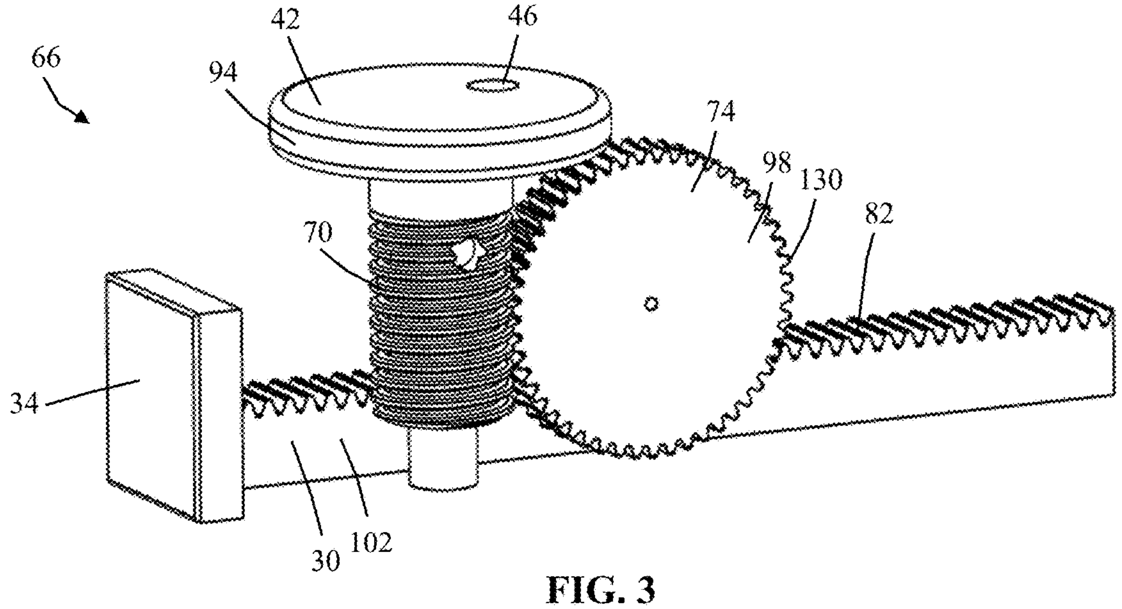

FIG. 3 is another perspective view of the transmission of the dose delivery device of FIG. 1A.

Figure 4:
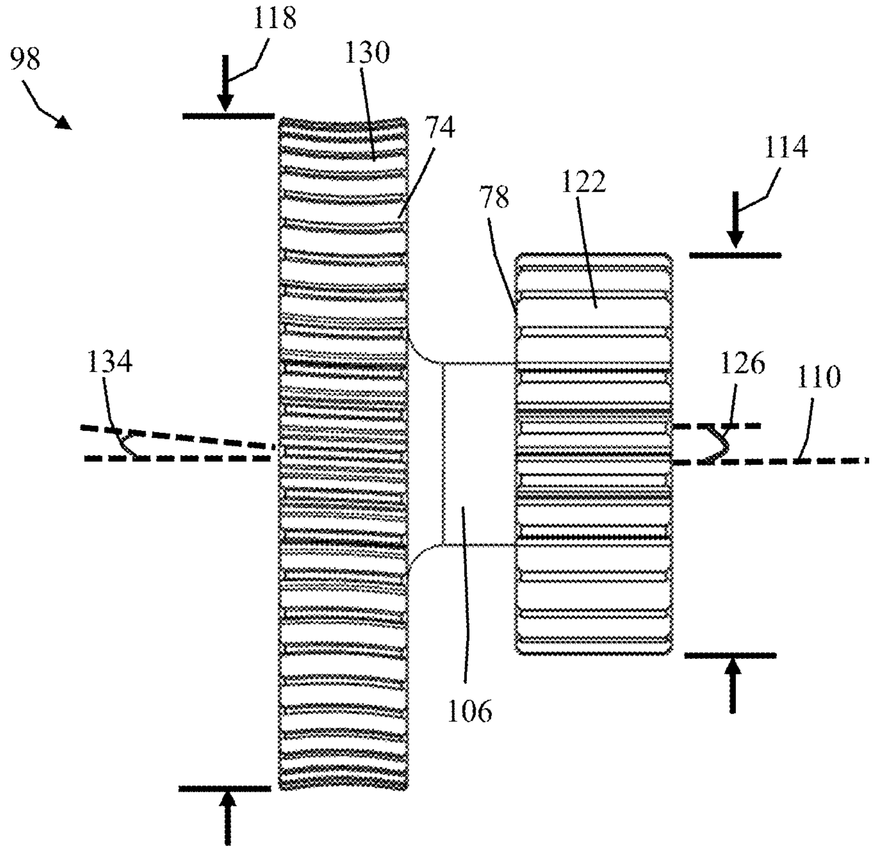

FIG. 4 is a side view of a component of the transmission of FIG. 2 comprising a worm gear and a pinion gear in fixed relationship.

Figure 5:
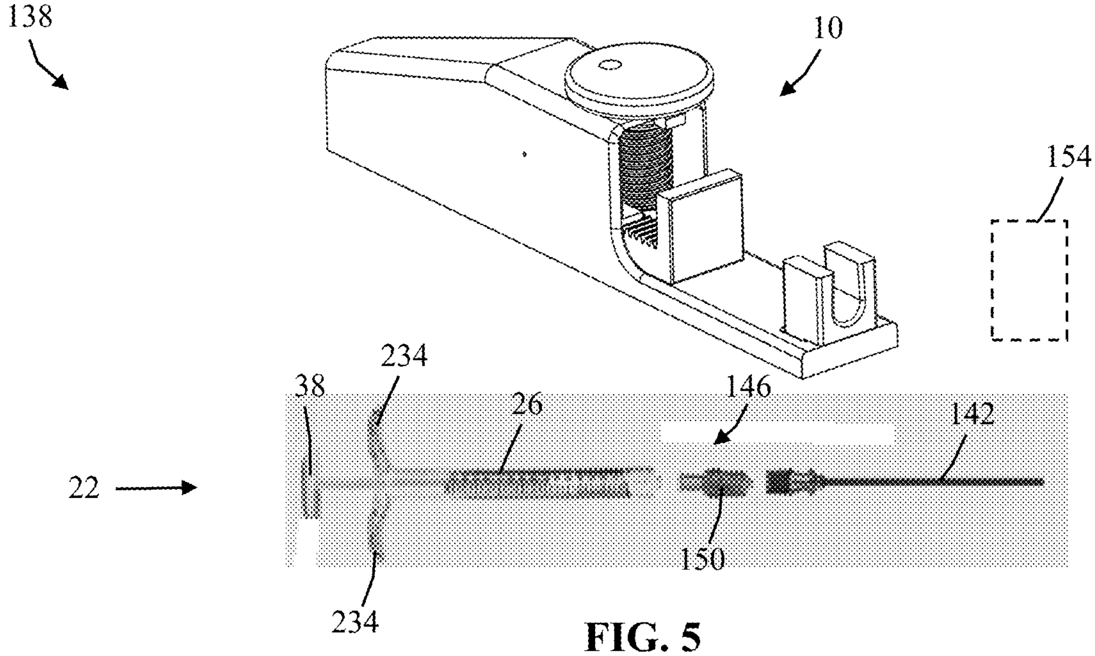

FIG. 5 is an illustration of a kit including a dose delivery device, a needle-syringe, and a cytotoxic or cytostatic drug, solvent and polymer.

Figure 6:
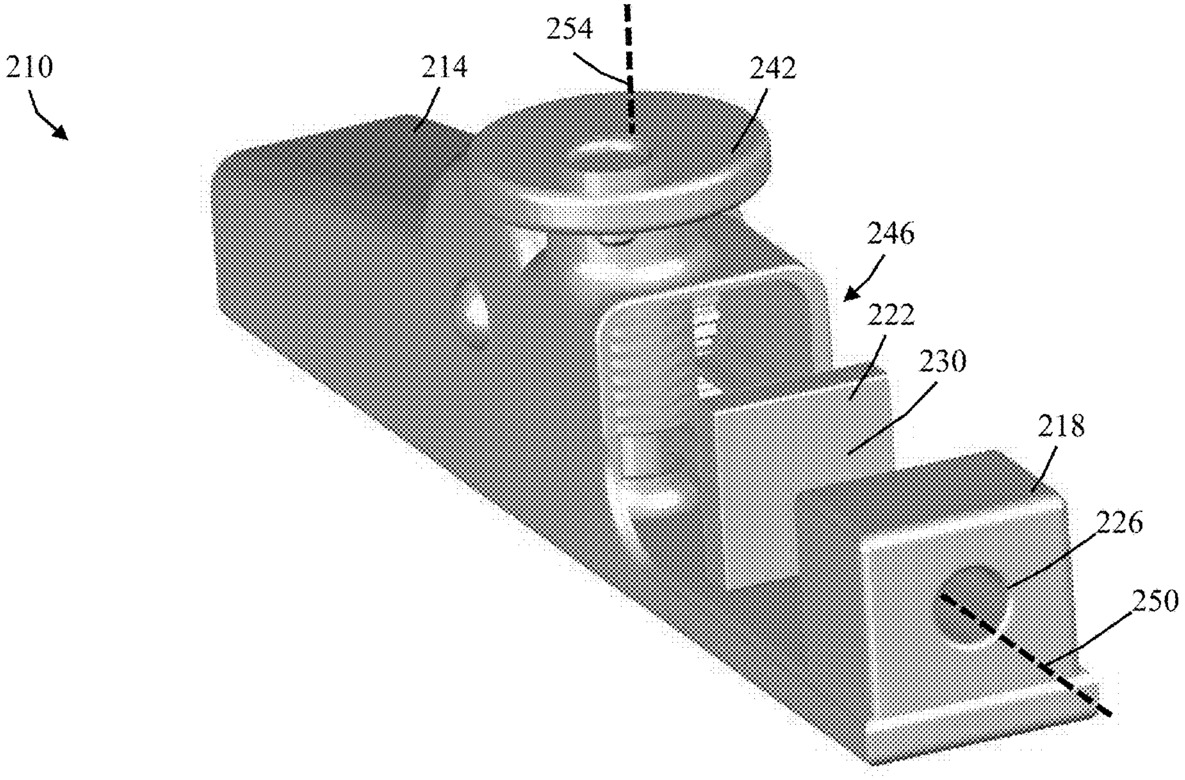

FIG. 6 is a perspective view of a dose delivery device.

Figure 7:
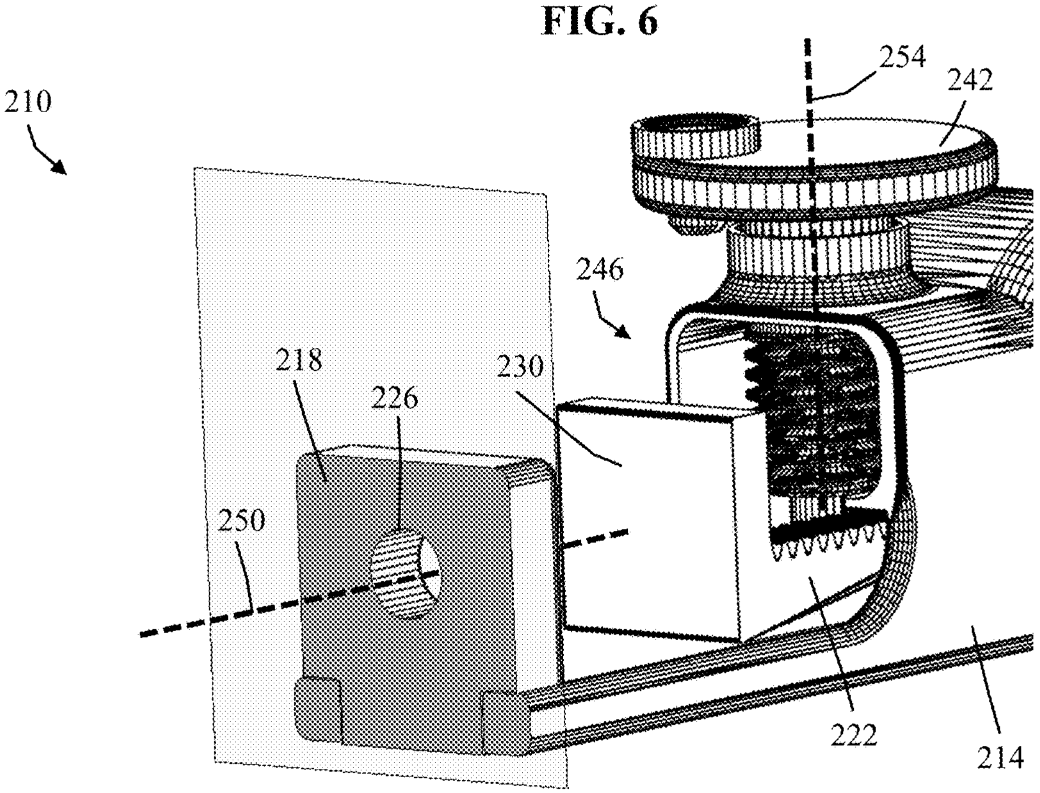

FIG. 7 is a perspective cross-sectional view of the dose delivery device of FIG. 6.

Figure 8:
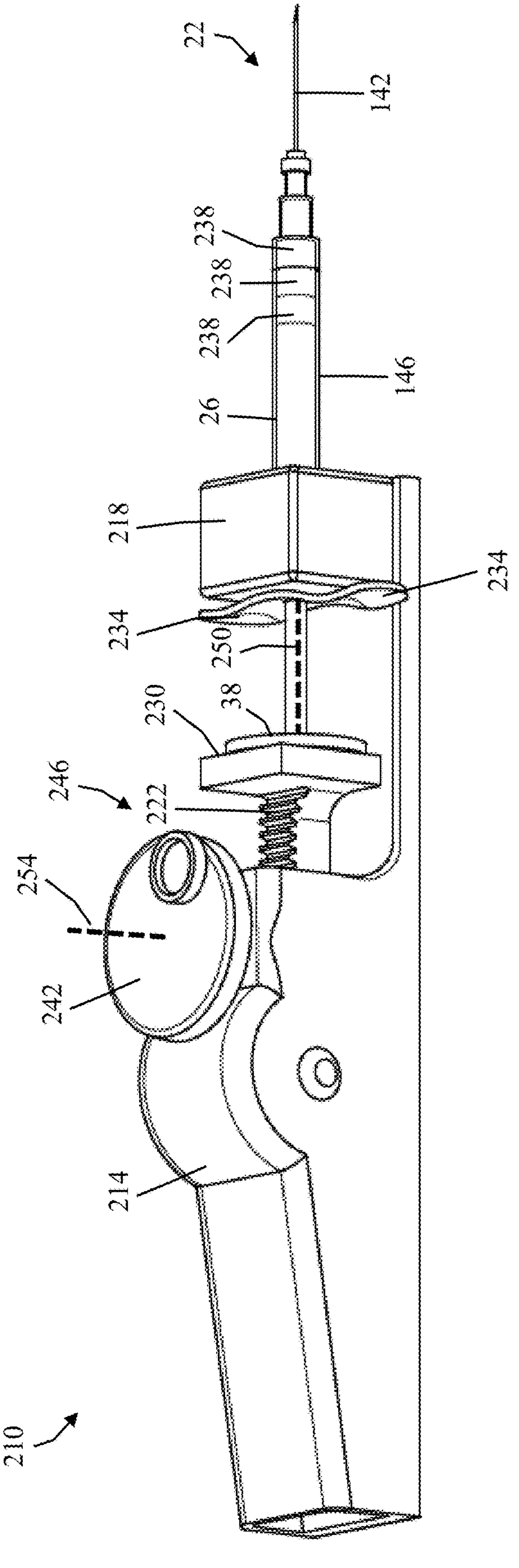

FIG. 8 is a perspective view of a needle-syringe mounted in the dose delivery device of FIG. 6.

Figure 9:
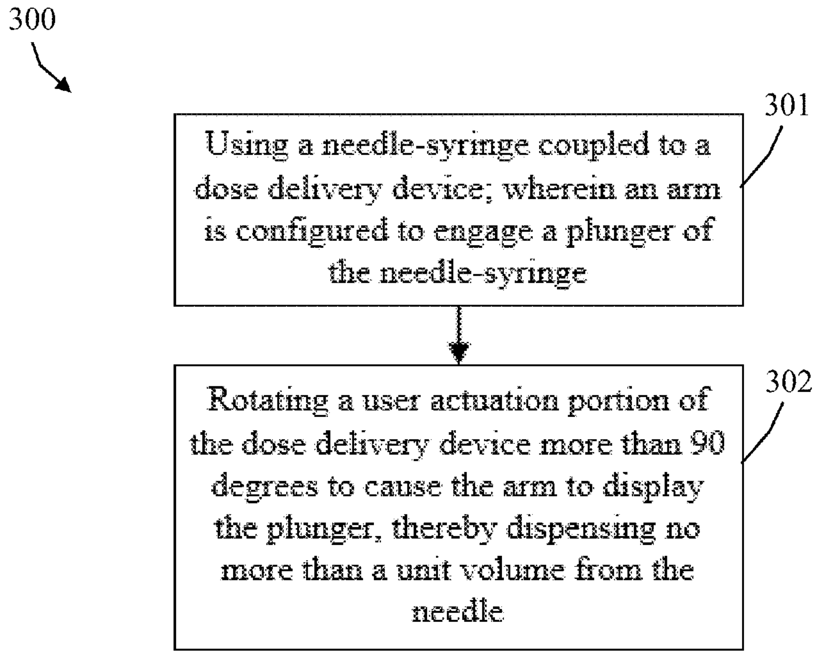

FIG. 9 is a flow chart of a method for treating a prostate.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter.

The terms "about" or "approximately" is defined herein as 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, dl is about d2 means dl is 30%, 20%, 15%, 10%, 5%, 4%, 3%, 2%, 1.5%, 1%, 0% or between 1-2%, 1-3%, 1-5%, or 0.5%-5% different from d2. If dl is a mean value, then d2 is about d1 means d2 is within a one-sigma, two-sigma, or three-sigma variance from dl. It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately." Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The term "unit volume" as used herein refers to the maximum volume (v) of composition for an individual injection or implantation when treating the patient's prostate. In most cases there is a plurality of unit volumes of a composition when treating the patient during a single treatment session. It is understood that this "treating the patient" or a single treatment session refers to a treatment that occurs within 1-2 hours, less than an hour, or within a 24 hour period. As such, a single treatment session or treating the patient by implanting a plurality of unit volumes takes place within an hour, or within a 24 hour period. A "unit volume" is defined as a volume of 5 μl to 10 μl, 10 μl to 25 μl, 25 μl to 50 μl, 50 μl to 100 μl, or 25 μl to 500 μl.

For example, there can be n=2, 3, 4, 5, 6, or more, depending on the size of the prostate, which can be determined from ultrasound and/or MRI imaging prior to treatment. Herein, n is the number of unit volumes. The larger the size of the prostate, generally speaking, the higher the number of unit dispensed from a needle at different locations of the prostate. It was found volumes in pre-clinical studies that a prostate treatment using a unit volume of 0.05 ml to 0.1 ml of composition can result in significant reduction in prostate size over a 90 day period. Moreover, it is believed that a unit volume of 5 μl to 10 μl, 10 μl to 25 μl, 25 μl to 50 μl, 50 μl to 100 μl, or 25 μl to 500 μl will also produce positive clinical outcomes with no adverse indications.

The term "drug" or "therapeutic agent" as used herein is defined as a therapeutic substance, used in the prevention, diagnosis, alleviation, treatment, or cure of disease. Unless stated otherwise, "drug" and "therapeutic agent" have the same meaning.

In certain embodiments, the one or more therapeutic inhibitor agents are selected from a cytostatic or anti-proliferative agent, a mTOR/PI3K dual, a mTORC1/mTORC2 dual inhibitor, a cytotoxic agent, a 5-alpha reductase inhibitor, an alpha blocker and/or smooth muscle cell relaxer, an anti-inflammatory agent, an anti-fibrotic agent, a non-steroidal antiandrogen, and antiandrogen antineoplastic agent.

The term "cytostatic" as used herein refers to a drug that is non-toxic to cells but does mitigate cell proliferation and permit cell migration. Cytostatic drugs may include without limitation rapamycin, sirolimus, everolimus, zotarolimus, myolimus, temsirolimus, tacrolimus, macrolide antibiotics, ridaforolimus, biolimus, novolimus, deforolimus, structural derivatives and functional analogues of rapamycin and any macrolide immunosuppressive drug. mTOR/PI3K dual inhibitors may also be utilized including dactolisib, BGT226, SF1126, PKI-587, and NVPBE235, mTORC1/mTORC2 dual inhibitors may also be utilized including sapanisertib, AZD8055, AZD2014 as derived from morpholino pyrazolopyrimidine.

The term "cytotoxic" as used herein refers to a drug that inhibits cell growth and proliferation such as chemotherapeutics. These drugs may include but are not limited to paclitaxel, taxanes, protaxel, vincristine, etoposide, nocodazole, indirubin, anthracycline derivatives, daunorubicin, daunomycin, tauromustine, bofumustane, carboplatin, carmustine, cisplatin, docetaxel, carbazitaxel, fluorouracil, gemcitabine, mitomycin, procarbazine, and plicamycin. These drugs may also be apoptotic such as TGF, topoisomerase inhibitors, including, 10-hydroxycamptothecin, irinotecan, and doxorubicin.

The term "sustained release formulation (SRF)" as used herein refers to a substance for treating BPH, the substance including a drug (or drugs), solvent for the drug and carrier for the drug(s) or drug carrier comprising a polymer composition administered to the target tissue in liquid, gel or solid form using a delivery vehicle, such as a needle syringe, whereupon local delivery of the composition (comprising the SRF) to the target tissue the SRF is effective in producing a sustained release of the drug(s) to the targeted tissue of the prostate, thereby producing an efficacious result over a period of time, e.g., from 14 days, 30 days, 1 to 3 months, up to 6 months, up to 12 months, or up to 2 years following treatment and with minimal uncontrolled drug diffusion. Other substances may also be present in the composition (e.g., an ultrasound/echoing enhancing medium or other imaging enhancing depending on the imaging modality used). A programmed, sustained release of, e.g., from 14 days or 1 to 12 months for substantially all of the drug to dissipate from the carrier is achieved by selection of drug carrier (polymer composition) and/or modifying the morphology and mechanical properties, the polymer/drug ratio, and controlling the physical shape/dimensions (volume) of the SRF and/or composition that is delivered to the target tissue. Other factors influencing a release rate are described in greater detail, below.

The term "composition" as used herein means a product of mixing or combining various elements or ingredients. Whenever the word "composition" is used, it will be understood that the composition comprises an SRF. The term "polymer composition" however is not a composition that comprises the SRF.

The term "absolute viscosity" as used herein means the viscosity measured relative to the viscosity of a known substance. Unless stated otherwise "absolute viscosity" (as compared to inherent viscosity) is represented by the symbol P. Absolute viscosities may be measured using a calibrated digital rotational viscometer spindle (no. 1 size) with 10 mL solutions in 40 ml polypropylene vials with an approximately 50% submerged spindle solution contact, with measurements made at room temperature conditions.

The term "total volume" of composition (i.e., the sum of n unit volumes of composition injected into the prostate during a single treatment session, defined as within 1-2 hours of, or within 24 hours of each other) is the total volume of composition administered to the patient and expected to produce a programmed, sustained release and efficacious outcome when treating BPH. This programmed, sustained release and efficacious outcome may be measured using the International Prostate Symptom Score (IPSS), or more generally relieving lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia. A total volume is ideally expected to produce more than a 10% reduction in prostate volume, or more than a 20% reduction in prostate volume, or morphological change the reduces pressure on the urethra. According to the pre-clinical study using canine models, prostate volumes were reduced by up to 30% over a 30 to 180 day period (canine prostate sizes ranged from 19.5 to 44.1 cc, with average being 30 cc at treatment, and averages being 10 cc at 30 and 90 days after treatment). In some embodiments, the number, n, of a unit volume, v, needed to attain a total volume of composition for prostate treatment is related to the prostate volume, PV as $n=PV/(200^*v)$ (rounded to nearest integer). For example, a prostate volume of 30 cc, and unit volume of 0.07 ml gives 2.14, which then gives n=2.

The term "target tissue" as used herein is defined as prostate tissue to include the transition zone, median lobe, left lobe, right lobe, peripheral zone and central zone of the prostate, anterior prostate, and the prostate.

The following are examples of the polymer naming nomenclature appearing in the listing of additional disclosed embodiments following the detailed description. Other examples not explicitly spelled out here use the same rationale: PLGA8515A (0.3 dl/g) means poly(lactide-co-glycolide) with a monomer ratio of 85/15, end capped with an acid group (A), and an inherent viscosity of 0.3 dl/g; and PLGA6535E (0.5 dl/g) means poly(lactide-co-glycolide) with a monomer ratio of 65/35, end capped with an ester groups (E), and an inherent viscosity of 0.5 dl/g; and PLGA5050A (0.2 dl/g) means poly(lactide-co-glycolide) with a monomer ratio of 50/50, end capped with an acid group (E), and an inherent viscosity of 0.2 dl/g; and Poly (lactide-co-glycolide) is typically poly(D,L-lactide-co-glycolide) but could also be e.g. any or a mixture of poly(D, L-lactide-co-glycolide), poly(D-lactide-co-glycolide), and poly(L-lactide-co-glycolide).

Unless stated otherwise, weights are given in grams ("g") or milligrams ("mg"), molecular weight in kilo-Daltons ("kDa"), volume in microliters ("L") or milliliters ("mL"), and viscosity units are expressed as inherent viscosity (i.e., the ratio of the natural logarithm of the relative viscosity to the mass concentration of the substance, such as a polymer. The unit of inherent viscosity is deciliters per gram (dL/g). A different measure of viscosity is intrinsic viscosity, which is a measure of a solute's contribution to the total viscosity. Another viscosity is dynamic viscosity or absolute viscosity, the units of which are centimeter-gram-seconds, also known as centipoise (cP).

The disclosure is generally directed to achieving a local delivery of a sustained release formulation at a specification for efficacious treatment of a target tissue associated with the prostate. A related disclosure found in U.S. Pat. No. 12,090,136 incorporated herein by reference in its entirety for all purposes.

With reference to FIG. 1A, a dose delivery device 10 (also referred to as a "dose guide" device) includes a housing 14 and a holder 18 configured to receive a portion of a needle-syringe 22 (e.g., a barrel 26 of the needle-syringe 22, FIGS. 5 and 8). In the illustrated embodiment, the holder 18 is a U-shaped cradle that creates a snap-fit or elastic connection with the needle-syringe 22. The elastic retention of the needle-syringe 22 by the holder 18 resists the needle-syringe

22 from being inadvertently dislodged during use. In some embodiments, the holder 18 is removably attached to the housing 14 and may be replaced with another holder 18 of a different size to accommodate a different sized needle-syringe.

With continued reference to FIG. 1A, the dose delivery device 10 includes an arm 30 at least partially extending from the housing 14. The arm 30 includes a surface 34 configured to engage a portion of the needle-syringe 22 (e.g., a plunger 38 of the needle-syringe 22). The dose delivery device 10 further includes an actuation member 42 movable with respect to the housing 14. In the illustrated embodiment, the actuation member 42 is a circular wheel with a dimple 46 formed on a top surface 50. As detailed further herein, the arm 30 moves along a translation axis 54 in response to user actuation of the actuation member 42 about a rotational axis 58. For example, with reference to FIG. 1B, rotation of the actuation member 42 about the rotational axis 58 causes the arm 30 to move along the translation axis 54. Specifically, the arm 30 moves towards the holder 18 in response to user actuation of the actuation member 42 about the rotational axis 58. In the illustrated embodiment, the translation axis 54 is orthogonal to the rotational axis 58. In some embodiments, the translation axis 54 is parallel to the to the rotational axis 58. In some embodiments, the translation axis 54 is obtuse or acute to the rotational axis 58. In another embodiment the worm rotation axis can be parallel to the pinion or worm gear rotation axis. In this embodiment a user may advance the needle-syringe plunger by directing, e.g., the thumb, in a forward (distal) or rearward (proximal) motion to rotate the worm. In this embodiment there may also be a catch or stop to indicate to the user when the worm has rotated sufficiently to dispense one unit volume from the needle.

With reference to FIGS. 1A and 1B, the dose delivery device 10 is configured to be held by a user hand and the actuation member 42 is configured for actuation by a user thumb of the user hand. In the illustrated embodiment, the actuation member 42 is positioned on a top surface 62 of the housing 14, and the top surface 62 does not intersect the translation axis 54 of the arm 30. In some embodiments, the arm 30 translates approximately 1.27 mm along the translation axis 54 in response to approximately 360 degrees of rotation of the actuation member 42 about the rotational axis 58. In some embodiments, the arm 30 translates approximately 2.5 mm along the translation axis 54 in response to approximately 180 degrees of rotation of the actuation member 42 about the rotational axis 58. As discussed in greater detail herein, the arm 30 translates a precise distance along the translation axis 54 to act on the plunger 38 of the needle-syringe 22 to advantageously dispense a precise volume from the needle-syringe 22. As such, the present disclosure provides for accurate and precise spatial and volumetric implantation of multiple small unit volumes of a SRF (e.g. RT-310) in an enlarged prostate, for example, for treatment of lower urinary tract symptoms secondary to benign prostatic hyperplasia.

With reference to FIGS. 2 and 3, the dose delivery device 10 comprises a one-way transmission 66 including a worm 70 coupled to the actuation member 42, a worm gear 74 engaged with the worm 70, a pinion gear 78 fixed to the worm gear 74, and a gear rack 82 formed on the arm 30. In the illustrated embodiment, the pinion gear 78 is engaged with (e.g., enmeshed with) the gear rack 82 on the arm 30.

As used here, the term "one-way transmission" refers to a transmission configured to do mechanical work in one direction but not the opposite direction. The arm 30 will move in the opposite direction only by rotating the actuation member 42 in the opposite direction. A force applied to the arm by fluid back-pressure will not displace the arm rearward. Referring briefly to FIG. 8, an actuation member 242 rotated clockwise will advance a surface 230 of an arm 222 in a first translational direction causing the syringe plunger 38 to move towards the needle 142. But any opposing force applied to the surface 230 (fluid backpressure) will not cause the arm 30 to move in the opposite direction. The only way the surface 230 may be moved in the opposite direction will be by rotating the actuation member 242 counterclockwise. Fluid backpressure on the plunger 38 will not be able to move the arm 222. Advantageously, the one-way transmission 66 prevents the dose delivery device 10 from being back-driven by pressure in the needle-syringe 22. As such, backpressure of the needle-syringe applied to the arm 30 will not displace the arm 30 in the second direction 90. Translational motion is constrained unless the actuation member 42 is rotated because the worm 70 and the worm gear 74 are orientated at approximately 90 degrees to each other. Therefore, only the clockwise or counterclockwise motion of the worm 70 can produce translational motion of the arm 30. In some embodiments, the one-way transmission 66 includes a gear ratio of approximately 50:1. In some embodiments, the one-way transmission 66 includes a gear ratio of approximately 10:1. In some embodiments, the one-way transmission 66 includes a gear ratio with a range of approximately 2:1 to approximately 100:1. The gear ratio between the worm and the worm gear is a ratio of the number of revolutions of the worm to one revolution of the worm gear. Therefore, for a gear ratio of 50:1, the worm completes 50 revolutions for every 360 degrees of rotation of the worm gear. Alternatively, with the pinion gear fixed to the worm gear, a 50:1 gear ratio means the worm completes 50 revolutions for one full revolution (360 degrees) of rotation of the pinion gear.

Advantageously, the disclosed dose delivery device 10 enables precise dispensing of unit volumes as small as approximately 5 microliters, and backpressure does not move the plunger 38 as a result of the one-way transmission 66. Furthermore, the gear ratio of the one-way transmission 66 enables a user to easily rotate the actuation member 42 across a wide range of angles with one hand and little or no resistance.

With continued reference to FIGS. 2 and 3, the dose delivery device 10 of the illustrated embodiment incorporates the one-way transmission 66 and comprises a first component 94 comprising the worm 70 and the actuation member 42, a second component 98 comprising the worm gear 74 and the pinion gear 78 in fixed relationship, and a third component 102 comprising the arm 30 including the gear rack 82. The worm 70 is coupled to the actuation member 42 (e.g., the first component 94) for co-rotation about the rotational axis 58. In the illustrated embodiment, rotation of the worm 70 causes the worm gear 74 and the pinion gear 78 (e.g., the second component 98) to rotate at the same rotation rate to thereby cause the surface 34 of the arm 30 to translate along the translation axis 54 (e.g., extend towards the holder 18).

With reference to FIG. 4, the pinion gear 78 is fixed to the worm gear 74 for co-rotation by an intermediate shaft 106. In other words, the pinion gear 78 is affixed to the worm gear 74 for co-rotation about a gear axis 110. In the illustrated embodiment, the gear axis 110 is orthogonal to the rotational axis 58 of the actuation member 42, and orthogonal to the translation axis 54 of the arm 30. In the illustrated embodiment, the pinion gear 78 has a pinion diameter 114 and the worm gear 74 has a worm diameter 118, and the worm diameter 118 is larger than the pinion diameter 114. In the illustrated embodiment, the pinion gear 78 has a plurality of gear teeth 122 with a helix angle 126 of approximately 0 degrees. In some embodiment, the pinion gear 78 has gear teeth with a helix angle within a range of approximately 0 to approximately 5 degrees. In some embodiments, the pinion gear 78 has gear teeth with a helix angle within a range of approximately 0 to approximately 10 degrees. In the illustrated embodiment, the worm gear 74 has a plurality of gear teeth 130 with a helix angle 134 within a range of approximately 5 degrees to approximately 10 degrees. In some embodiments, the worm gear 74 has gear teeth with a helix angle within a range of approximately 1 degree to approximately 20 degrees.

With reference to FIG. 5, a kit 138 comprises a needle 142, a syringe 146 (the needle 142 and syringe 146 may be referred to collectively as a needle-syringe), and the dose delivery device 10. The syringe 146 includes a barrel 26 receivable within the holder 18. The syringe 146 also includes a plunger 38 that is positioned to engage the surface 34 of the arm 30 when the barrel 26 is received within the holder 18 (e.g., FIG. 8). In some embodiments, the syringe 146 includes a one-way valve 150. A needle-syringe 22 is formed when the needle 142 and the syringe 146 are assembled together. In some embodiments, the syringe 146 is a 1 mL syringe and the needle 142 is a Chiba needle or alternative needle. Advantageously, the dose delivery device 10 is configured to receive and operate on a wide range of needle and syringe sizes.

In some embodiments, the kit 138 further includes a cytotoxic or cytostatic drug, solvent and polymer 154. In some embodiments, the cytotoxic or cytostatic drug, solvent and polymer 154 are provided for being combined by a user to form a sustained release formulation (SRF). The SRF is loaded into the syringe 146, the needle 142 is attached to the syringe 146, and the barrel 26 of the syringe 146 is placed in the holder 18 of the dose delivery device 10. In some embodiments, the kit 138 further includes a formulation (e.g., composition, or SRF) having a viscosity within a range of approximately 100 centipoise to approximately 500 centipoise.

With reference to FIG. 6, a dose delivery device 210 is illustrated with a housing 214, a holder 218 configured to receive a first portion (e.g., the barrel 26) of the needle-syringe 22, and an arm 222 at least partially extending from the housing 214. The dose delivery device 210 is similar to the dose delivery device 10 disclosed herein with the differences described in further detail. As such, the description herein referring to the dose delivery device 10 also refers to the dose delivery device 210, and vice versa, unless explicitly noted otherwise.

With reference to FIG. 7, the holder 218 includes a circular channel 226 to receive the barrel 26 of the needle-syringe 22, and the holder 218 is removeable from the housing 214. In some embodiments, the holder 218 is attached to the housing 214 with a snap-fit attachment. As such, alternate holders with various sized channels can be attached to the housing according to the corresponding size of the needle-syringe. For example, a user may insert the syringe 146 into the channel 226 formed by the removable holder 218, and then attach the holder 218 to the housing 214 via a snap-fit connection.

With reference to FIG. 8, the needle-syringe 22 is illustrated loaded into the dose delivery device 210. The arm 222 includes a surface 230 configured to engage the second portion (e.g., the plunger 38) of the needle-syringe 22. The syringe 146 includes wings 234 that abut the holder 218 to prevent the barrel 26 from displaying when the plunger 38 is pushed by the arm 222. The needle-syringe 22 shown is one example of one of many needle-syringe designs usable with the dose delivery devices disclosed herein.

In the illustrated embodiment, the needle-syringe 22 comprises a plurality of unit volumes 238 of a composition consisting of a drug, polymer and solvent. In some embodiments, each of the plurality of unit volumes 238 is the same volume and is within a range of approximately 25 μl and approximately 100 μl. The dose delivery device 220 includes an actuation member 242 movable with respect to the housing 214 and a one-way transmission 246 coupled between the actuation member 242 and the arm 222. The arm 222 moves along a translation axis 250 in response to user actuation of the actuation member 242 about a rotational axis 254. In the illustrated embodiment, the dose delivery device 210 is calibrated such that a pre-set amount of rotation (e.g., approximately 180 degrees) of the actuation member 242 about the rotational axis 254 advances the arm 222 by a distance along the translation axis 250 corresponding to one of the plurality of unit volumes 238.

Advantageously, the needle-syringe 22 dispenses no more than one of the plurality of unit volumes 238 with an volumetric accuracy of at least 90% in response to the actuation member 242 rotating more than 90 degrees about the rotational axis 254. In some embodiments, the needle-syringe 22 dispenses no more than one of the plurality of unit volumes 238 with an accuracy of at least 90% in response to the actuation member 242 rotating a total rotation within a range of approximately 180 degrees and approximately 360 degrees about the rotational axis 254. In some embodiments, the needle-syringe 22 dispenses no more than one of the plurality of unit volumes 238 with an accuracy of at least 90% in response to the actuation member 242 rotating a total rotation within a range of approximately 90 degrees to approximately 360 degrees, 360 to 720 degrees, or 90 to 720 degrees about the rotational axis 254. As such, the dose delivery device 210 is advantageously configured to deliver a unit volume within a high accuracy for rotations of the actuation member greater than 90 degrees. In one embodiment, a user can implant 4-7 50 μl implants per syringe (e.g., 200-350 μl after needle priming). In another embodiment, a user can implant 8-12 25 μl implants (e.g., 200-300 μl after needle priming).

With reference to FIG. 9, a method for treating a prostate is illustrated. The method 300 includes (STEP 301) using a needle-syringe coupled to a dose delivery device having a user actuation portion, a one-way transmission, and an arm. The arm is configured to engage a plunger of the needle-syringe to dispense no more than a unit volume from the needle. The method 300 further includes (STEP 302) rotating the user actuation portion more than approximately 90 degrees to cause the arm to displace the plunger, thereby dispensing the unit volume from the needle. Advantageously, no more than a unit volume is dispensed from the needle in response to rotating the user actuation portion more than 90 degrees. In some embodiments, the unit volume is within a range of approximately 5 μl to approximately 100 μl. In some embodiments, the unit volume is within a range of approximately 25 μl to approximately 50 μl. As detailed herein, in some embodiments, the method 300 for treating the prostate treats benign prostatic hyperplasia (BPH).

The dose delivery devices disclosed herein mitigate the risk of implanting too much or too little of a high viscosity composition. In addition, the dose delivery device reduces the risk of implanting composition at the wrong location in the prostate because the health professional does not need to visually focus on the small needle-syringe graduations to visually meter doses. In some embodiments, the delivery dose device includes a tactile or audible feedback to dispense unit volumes, while the health professional focuses their attention on a live ultrasound image tracking the needle through the prostate, for example.

The dose delivery devices disclosed herein is utilized to meter and deliver each unit volume 5-50 microliter of SRF (paclitaxel) prostate implant, a minimally invasive, intraprostatic sustained release paclitaxel therapy with bioabsorbable polymer implant. In some embodiments, the intraprostatic delivery is guided by ultrasound imaging using a transperineal approach ideally utilizing a stepper stabilizer for the ultrasound probe allowing the physician to use one or both hands for delivery of the RT-310 implants. The dose delivery device is intended for the user to deliver multiple 5-50 μL RT-310 implants accurately and precisely, without looking at the device. This maximizes the physician's ability to focus on the ultrasound imaging and reduces potential hazards such as incorrect implant volume and/or delivery to non-target tissue. Alternatively, it can be used for transrectal delivery. Alternatively, the technology is referred to as IntraProstatic Drug Elution (IPDE).

K-Injectate Rating (KIR). The method includes dispensing one or more unit volumes of composition from the needle-syringe at a respective one or more target tissue locations of the prostate. The apparatus is characterized by its K-injectate Rating (KIR) defined by the following relationship:

$$KIR = \frac{\mu L^2}{vD}(10^{-6})$$

Where μ is the absolute viscosity (cP) of the composition, L is the needle length (cm) measured from the needle tip to the end of the needle hub, D is the needle lumen diameter (cm), and v is a unit volume ($cm^3$ or cc) of the composition contained in the syringe barrel. Each unit volume represents a maximum volume of the composition dispensed at a single location of the target tissue. In some embodiments the syringe holds a plurality of unit volumes, which enables the dispensing of a unit volume at each of a corresponding plurality of discrete locations of the target tissue.

There is also disclosed an apparatus for prostate treatment. The apparatus comprises a needle-syringe, a dose delivery device, and the composition contained within the syringe. The apparatus is adapted to deliver the composition in one or more unit volume increments to a target tissue, as defined by its KIR value. KIR values for the method, apparatus, medical device, and system according to the disclosure may range from between 10 and 1000, 10 and 300, or 40 and 400. The units of KIR are centipoise per unit area. Exemplary embodiments of a device satisfying the KIR criterion, summarized infra (minimal uncontrolled drug diffusion, sustained release and efficacy, and low volume/unit volume) are found in WO 2023/147080, FIGS. 3A, 3B, Table 2, herein incorporate by reference.

Prostate treatment according to the disclosure may be described as a prostate treatment having three characteristics: minimal uncontrolled drug diffusion, sustained release and efficacy, and a unit volume as defined herein. The KIR identifies the needle syringe capable of delivering these one or more unit volumes of a composition, in a safe, repeatable pattern by a health professional and without imposing significant compromises on the composition's ability to achieve minimal uncontrolled drug diffusion, sustained release and efficacy.

Accordingly, in one aspect, a treatment of prostatic hyperplasia tissue, as provided herein, includes the delivery of a drug or multiple drugs to the tissue in a sustained release manner using a needle syringe containing the SRF. The treatment may be used with, or in addition to treatments involving removal/ablation of tissue, and/or delivery of energy to the tissue and additionally the administering of various agents. Methods according to the disclosure may additionally, or alternatively, be administered after a treatment of BPH according to other methods.

Access to prostatic tissue may be achieved in a transurethral, transrectal or transperineal manner via an existing body orifice. It may be beneficial and less invasive to access the tissue by either transrectal or transperineal approaches. The advantages with a transrectal or transperineal approach include one or more (1) oral and/or local anesthesia application instead of general anesthesia, (2) less trauma to the urethra tract and less resulting side effects also reducing the need for catheterization, (3) faster recovery time for the patient, (4) familiar treatment for the urologist physician similar to prostate cancer biopsy. For access by transrectal or transperineal approach, guidance may be provided by ultrasound, x-ray, computed tomography, magnetic resonance imaging or other imaging modality. Ultrasound imaging may be beneficial given that ultrasound is utilized for prostate biopsy. The transrectal approach closely mirrors the present prostate ultrasound and biopsy techniques familiar to urologists. Transrectal and transperineal approaches both avoid interaction with the urethra, which limits the caustic effects of urethral procedures therefore minimizing side effects and dysuria associated with currently available BPH procedures.

The drug portion of the composition may be an anti-inflammatory, anti-proliferative, cytoreductive, cytostatic, and/or cytotoxic drug that would affect the prostate size and gland proliferation. The apparatus enables delivery of one or more drugs into the target tissue. Once delivered to the target tissue, the drug may then release from the SRF in a slow, sustained release fashion, optionally delivered as an initial burst of the drug, followed by a slow, sustained release of the drug to the target release. The amount or lack of burst and/or the "slow, sustained release" release period may depend on the drug delivered to the prostate, the SRF properties, and the KIR value, as will be appreciated in view of this disclosure. In some embodiments a slow, sustained release may occur over, e.g., a 24-hour period, 3-7 days, 1-4 weeks, 1 to 12 months, 3 months, 6 months, or 12 months.

In another aspect there is a system for treating BPH including a needle syringe, the sustained release formulation (SRF), and imaging device for locating a target tissue of the prostate. The imaging device, e.g., ultrasound, may be used both as a needle guide to the target tissue and for sizing the prostate. Once the prostate size is determined, the number, n, of unit volumes, v, for injection may be determined. A needle syringe according to the disclosure may hold one or a plurality of unit volumes dispensable from the needle to treat the prostate in a controlled manner, as determined by the KIR value for the syringe containing the composition. The KIR value is between 10 and 1000, 10 and 300, or 40 and 400.

In another aspect there is a method for making a medical device for treating the prostate, including the steps of combining at least one drug with at least one polymer carrier to form a composition comprising an SRF, wherein the composition is contained within a needle syringe, and wherein the needle syringe containing the composition has a KIR value of between 10 and 1000, 10 and 300, or 40 and 400.

When adopting this numerical range as a requirement for the syringe needle with composition, in addition to the required three characteristics for prostate treatment, a more effective SRF formulation is found, because the value addresses the deliverability problem and without unnecessarily compromising the SRF effectiveness. The numerical range is computed using the K-Injectate Rating or KIR, defined as follows:

$$KIR = \frac{\mu L^2}{vD}(10^{-6})$$

For a KIR between 40 and 400, with units of centipoise (cP) per unit area, one may conclude that the SRF can be reliably and consistently delivered in unit volume increments using a needle having a length L, lumen diameter D, a composition's absolute viscosity and a unit volume v. The KIR is defined for L from 10 to 30 cm, more preferably from 15 to 20 cm, a lumen diameter D of 0.06 cm, or between 0.06 and 0.08 cm, and in some embodiments 0.02 cm up to 0.12 cm. The needle's slenderness ratio (L/D) may be between 200 and 400, or between 250 and 350.

In some embodiments KIR may be between 10 and 1000. The higher ranges may be preferred in situations where a more delayed release rate and/or higher rate of gelation is desired, as well as smaller unit volumes. A higher KIR may also be preferred for a larger prostate where a longer needle is needed to access the prostate transrectally. In some embodiments KIR may be 10 to 300. A smaller KIR may be preferred for a smaller prostate where a shorter needle is needed to access the prostate, transperineally.

The lower end of the KIR range represents compositions that while relatively easy to dispense in small unit volumes (for a fixed needle length, e.g., 15 cm), have a minimal amount of viscosity representative of an SRF's ability to satisfy two of the characteristics for prostate treatment (efficacy, sustained release, and minimal uncontrolled drug diffusion), shorter needle lengths and higher unit volumes. The upper end of the KIR range in TABLE 3 represent (for a fixed needle length, e.g., 20 cm) compositions having higher viscosity, longer needle lengths and smaller unit volumes. For these compositions, the two characteristics for prostate treatment will be easily satisfied when the formulation is injected, but the viscosity, if any higher, might challenge the health professional's ability to deliver a total volume of composition in unit volume amounts, especially along a longer needle length. As such, the capabilities of the delivery device are limiting for high KIR values.

Treatment of BPH by a needle injection, in a small quantity (unit volume) at a plurality of locations in the target tissue, offers several benefits over other methods. Among the benefits are less invasive procedures leading to greater patient acceptance and less complications during patient treatment, less frequent procedures needed, and reduced incidence of drug affecting nearby tissue leading to such outcomes as adverse consequences for urinary or sexual function.

In one aspect, the disclosure includes a method for treating Benign Prostatic Hyperplasia (BPH) in a subject in need thereof, comprising: using a needle syringe containing a composition comprising a cytotoxic or cytostatic drug, a glycolide-based bioabsorbable copolymer, and a water soluble solvent capable of dissolving the drug and copolymer; and dispensing a total volume of the composition into a prostate to produce an efficacious outcome for treating BPH, including dispensing no more than a unit volume of the composition into a prostate at a first prostate location using the needle syringe, further comprising using an apparatus comprising the needle syringe and the composition, the apparatus having a KIR of between 10 and 1000, 10 and 300, or 40 and 400.

In one aspect, the disclosure includes a method of treating Benign Prostatic Hyperplasia (BPH) in a subject in need thereof, comprising using an apparatus comprising a needle syringe containing a composition comprising a cytotoxic or cytostatic drug, a glycolide-based bioabsorbable copolymer, and a water soluble solvent capable of dissolving the drug and copolymer, wherein the composition has an absolute viscosity, p, and the needle syringe has a needle length L with inner diameter D; and dispensing a plurality of unit volumes, v, of the composition at a respective plurality of different locations in the prostate using the needle syringe; wherein a unit volume is from 0.05 ml to 0.2 ml; wherein the plurality of unit volumes is equal to a total volume for treating BPH; and wherein the apparatus has a KIR of between 10 to 300 or 40 to 400 and KIR is defined as:

$$KIR = \frac{\mu L^2}{vD}(10^{-6}).$$

Minimally invasive treatment methods for benign prostatic hyperplasia (BPH) tissue. A system includes a sustained release formulation comprising a cytostatic or cytotoxic drug, and an applicator or delivery system for local delivery of a composition comprising or consisting essentially of the sustained release formulation to the prostate. The applicator containing the composition is characterized by a KIR value of between 40 and 400 Centipoise per unit area.

Access to prostatic tissue may be achieved in a transurethral or transrectal manner via an existing body orifice or through transperineal entry. It may be beneficial and less invasive to access the tissue by either transurethral, transrectal or transperineal approaches. The advantages with a transrectal or transperineal approach include but are not limited to: (1) oral and/or local anesthesia application instead of general anesthesia; (2) less trauma to the urethra tract and less resulting side effects also reducing the need for post procedure catheterization; (3) faster recovery time for the patient; (4) familiar treatment for the urologist physician similar to prostate cancer biopsy; and combinations thereof.

For access by transrectal or transperineal approach, guidance may be provided by ultrasound, x-ray, computed tomography, magnetic resonance imaging or other imaging modality. Ultrasound imaging may be beneficial given that ultrasound is routinely utilized for prostate biopsy. The transrectal and transperineal approaches closely mirrors the present prostate ultrasound and biopsy techniques familiar to urologists. Transrectal and transperineal approaches both avoid interaction with the urethra, which limits the caustic effects of urethral procedures, therefore minimizing side effects and dysuria associated with current BPH procedures.

Accordingly, in certain embodiments, the therapeutic agent is administered by injection through a rectum, a perineum, or an urethra of the subject.

A prostate treatment according to the disclosure may be described as a prostate treatment having the following characteristics:

(1) MINIMAL UNCONTROLLED DRUG DIFFUSION: Upon contact with the prostate or prostate tissue, the drug or therapeutic agent remains at the target tissue and little or no drug/agent diffusion takes place to possibly affect unintended, adjacent tissue, such as the urethra, bladder, or seminal vesicles;

(2) SUSTAINED RELEASE & EFFICACY: Enabling a controlled release of a drug over time in a sufficient total dose to achieve the efficacious result of reduced prostate size; and (3) LOW VOLUME: Delivery of the total volume to the prostate using a needle delivery device. This manner of delivery avoids causing additional acute pressure on the urethra, which may cause additional discomfort for the patients immediately after or shortly after the procedure. It also can be desirable to have a low volume injected at several discrete, nearby locations to achieve the targeted clinical outcome, as this can optimize diffusion of a hydrophobic drug relative to diffusion from a large volume injected in one location.

Accordingly, in some embodiments, the implant is administered by injection or implantation with a needle having a length from about 15 cm to about 20 cm, including about 15 cm, 16 cm, 17 cm, 18 cm, 19 cm, 20 cm, and 25 cm. In certain embodiments, the needle comprises a lumen having a diameter from about 0.02 cm to about 0.12 cm, including a diameter of about 0.02 cm, 0.03 cm, 0.04, cm, 0.05 cm, 0.06 cm, 0.07 cm, 0.08 cm, 0.09 cm, 0.10 cm, 0.11 cm, and 0.12 cm. In certain embodiments, the needle has a ratio of length divided by lumen diameter of between about 100 and 1000, including a ratio of length divided by lumen diameter of about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000, or, in some embodiments, between about 230 and 340, including 230, 235, 240, 245, 250, 255, 260, 265, 270, 275, 280, 285, 290, 295, 300, 305, 310, 315, 320, 325, 330, 335, and 340.

In certain embodiments, the composition is administered via a needle guided by ultrasound imaging. The imaging device, e.g., ultrasound, may be used both as a needle guide to the target tissue and for sizing the prostate. Once the prostate size is determined, the number, n, of unit volumes for injection may be determined. A needle syringe according to the disclosure may hold one or a plurality of unit volumes of composition dispensable from the needle to treat the prostate in a controlled manner.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

A validation study in a bench prostate model was conducted to verify the dose delivery device meets specifications and acceptance criteria. Specifically, a study was performed to verify and validate the dose delivery device for 25 and 50 microliters RT-310 (paclitaxel) unit volume prostate implants using a 20 G Chiba Needle with a length of approximately 20.0 cm or 15.0 cm, and a dose delivery device (PN 022)

Intraprostatic delivery is guided by ultrasound imaging using a transrectal or transperineal approach. The transperineal approach is ideally utilizing a stepper stabilizer for the ultrasound probe allowing the physician to use both hands for delivery of the RT-310 implants. The dose delivery device is intended for the user to deliver multiple 25 ul or 50 uL RT-310 implants accurately and precisely, with rotation of a wheel, without looking at the device. This maximizes the physician's ability to focus on the ultrasound imaging and reduces potential hazards such as incorrect implant volume and/or delivery to non-target tissue.

As used herein, RT-310 consists of paclitaxel, active pharmaceutical ingredient, poly(D,L-lactide-co-glycolide) (PLGA) (50:50) polymer, and N-methyl pyrrolidone (NMP) solvent in pre-filled syringes that are mixed prior to use. Product container closure consists of vacuum sealed foil pouches including oxygen absorber (for drug) and desiccant (for polymer) pouches packaged in a unit box. The dose delivery device is a dose repeater device designed to meter repeated small volume injections and designed to fit with the RT-310 drug product graduated syringe after mixing per package insert and prior to needle priming.

Appearance and Syringe Fit. The dose delivery device was designed with an internal worm gear mated to a user operated rotating thumbwheel and a plunger rod to displace the syringe plunger. The 5 mm PN 008 syringe barrel outer diameter is secured by pushing the syringe thumb grip flush with the polylactide plug as shown in FIG. 8.

Implant Delivery (Accuracy and Precision) Verification. Accuracy and precision of implant delivery via the dose delivery device was verified by volume measurement of syringe graduations and mass measurement of each dispensed volume on the analytical balance. Given the syringe inner barrel diameter is 0.20" (5.1 mm) a plunger displacement of 2.5 mm delivers each 50 microliter volume. The dose delivery device is designed to travel via indexing action on the plunger rod with each full 360 degree wheel rotation providing a rod displacement of 1.25 mm such that two clockwise delivery wheel rotations on the dose delivery device provide a displacement of 2.5 mm for a delivery volume of 50 microliters. The plunger rod is only movable via rotation of the wheel and otherwise does not have the ability to traverse forward or backward unintended. When the wheel is rotated counterclockwise the plunger can be disengaged and pulled back to remove the syringe.

RT-310 product was mixed and prepared according to the package insert and connected to a 20 G×20 cm Chiba Needle. The 20 cm needle length was also chosen as a worse case for higher needle resistance given the larger length than the 15 cm needle. Three testers tested two different dose delivery devices with a minimum of at least four full tests per each dose delivery device to verify delivery accuracy and precision with test details summarized in the following Tables.

Data for each test were analyzed and dispensed implant mass and volume were calculated from the difference of mass and syringe volume measurements recorded. Data are summarized in Table 3 per test and dose delivery device and Table 4 per tester.

TABLE 3

| Summary of dose delivery device accuracy and precision testing for a 50 µl unit volume | | | | | | | | | | | | | |
|---|---|---|---|---|---|---|---|---|---|---|---|---|---|
| Implant Dispense Mass (mg) | | | | | | | Implant Dispense Volume (µL) | | | | | | |
| #1 | #2 | Mean | SD | % RSD | P/F | Total | #1 | #2 | Mean | SD | % RSD | P/F | Total |
| 45.2* | 62.4* | NA | NA | NA | NA | 107.5 | 50 | 40 | 45 | 7 | 16 | Pass | 90 |
| 53.4 | 57.4 | 55.4 | 2.8 | 5.1 | Pass | 110.8 | 50 | 50 | 50 | 0 | 0 | Pass | 100 |
| 53.6 | 58.7 | 56.1 | 3.6 | 6.4 | Pass | 112.3 | 50 | 50 | 50 | 0 | 0 | Pass | 100 |
| 49.6 | 61.7 | 55.7 | 8.6 | 15.4 | Pass | 111.3 | 50 | 50 | 50 | 0 | 0 | Pass | 100 |
| 54.4 | 59.4 | 56.9 | 3.5 | 6.2 | Pass | 113.8 | 50 | 50 | 50 | 0 | 0 | Pass | 100 |
| | SN001 Mean | 56.0 | | | Mean | 108.0 | | SN001 Mean | 49.0 | | | Mean | 98 |
| | SN001 SD | 0.7 | | | SD | 2.3 | | SN001 SD | 2.2 | | | SD | 4 |
| | SN001 % RSD | 1.2 | | | % RSD | 2.1 | | SN001 % RSD | 4.6 | | | % RSD | 5 |
| 48.1 | 57.2 | 52.7 | 6.5 | 12.3 | Pass | 105.3 | 50 | 50 | 50 | 0 | 0 | Pass | 100 |
| 52.1 | 56.3 | 54.2 | 3.0 | 5.5 | Pass | 108.3 | 50 | 50 | 50 | 0 | 0 | Pass | 100 |
| 54.1 | 58.6 | 56.3 | 3.2 | 5.7 | Pass | 112.6 | 50 | 50 | 50 | 0 | 0 | Pass | 100 |
| 54.6 | 56.5 | 55.6 | 1.3 | 2.4 | Pass | 111.2 | 50 | 50 | 50 | 0 | 0 | Pass | 100 |
| 54.1 | 29.8** | NA | NA | NA | NA | NA | 50 | 25** | NA | NA | NA | NA | NA |
| | SN002 Mean | 54.7 | | | Mean | 112.5 | | SN002 Mean | 50.0 | | | Mean | 100 |
| | SN002 SD | 1.6 | | | SD | 1.0 | | SN002 SD | 0.0 | | | SD | 0 |
| | SN002 % RSD | 3.0 | | | % RSD | 0.9 | | SN002 % RSD | 0.0 | | | % RSD | 0 |

TABLE 4

| Summary of dose delivery device accuracy and precision testing for a 50 µl unit volume | | | | | | | | | |
|---|---|---|---|---|---|---|---|---|---|
| Implant Dispense Mass (mg) | | | | | Implant Dispense Volume (uL) | | | | |
| n | Mean | SD | % RSD | P/F | n | Mean | SD | % RSD | P/F |
| 6 | 55.8 | 2.8 | 5.0 | Pass | 8 | 49 | 4 | 7 | Pass |
| 6 | 55.7 | 2.1 | 3.9 | Pass | 6 | 50 | 0 | 0 | Pass |
| 5 | 54.1 | 5.6 | 10.3 | Pass | 5 | 50 | 0 | 0 | Pass |
| 17 | 55.3 | 3.5 | 6.3 | Pass | 19 | 50 | 2 | 4 | Pass |
| 6 | 55.8 | 2.8 | 5.0 | Pass | 8 | 49 | 4 | 7 | Pass |
| 6 | 55.7 | 2.1 | 3.9 | Pass | 6 | 50 | 0 | 0 | Pass |
| 5 | 54.1 | 5.6 | 10.3 | Pass | 5 | 50 | 0 | 0 | Pass |
| 17 | 55.3 | 3.5 | 6.3 | Pass | 19 | 50 | 2 | 4 | Pass |

TABLE 5

| Summary of dose delivery device accuracy and precision testing for a 25 µl unit volume | | | | | | | |
|---|---|---|---|---|---|---|---|
| Dose Guide PN022 | | Implant Volume (µL) | | | | | |
| RevB LN 241125 SN | Product | Mean | Min. | Max. | StDev | % RSD | P/F |
| 001 | RT-310 | 24 | 20 | 26 | 2 | 9 | Pass |
| 002 | | 25 | 23 | 27 | 1 | 3 | Pass |
| 003 | | 25 | 23 | 27 | 1 | 5 | Pass |
| 004 | | 24 | 15 | 28 | 4 | 16 | Pass |
| 005 | | 23 | 16 | 28 | 4 | 18 | Pass |
| 006 | | 25 | 21 | 29 | 2 | 8 | Pass |
| Grand Mean | | 24 | | | | | |

A total of 10 tests were completed including 5 tests for different dose delivery devices per Table 3 and Table 4 for 50 µl. One of the dose delivery devices dispensed mean amounts of RT-310 of 56 mg (1.2% RSD) and 49 microliter (0% RSD) while another dose delivery device dispensed mean amounts of RT-310 of 55 mg (1.6% RSD) and 50 microliter (0% RSD). A total of 6 tests were completed including 6 tests for different dose delivery devices per Table 5 for 25 µl.

Implant Delivery Validation. User validation testing of RT-310 dose delivery device was performed in two separate tests by a board certified physician.

RT-310 product was mixed and prepared according to the package insert and connected to the 20 G×20 cm Chiba Needle.

Physician 1, a radiation oncologist evaluated the transperineal implantation of RT-310 using the dose delivery device in a prostate bench model. Physician 1 positioned the echogenic needle in the prostate model then performed transperineal implantation During delivery the implants exhibited an echogenic appearance potentially due to the precipitated implant (drug and polymer precipitation) having a size slightly larger than the needle tract (FIG. 4).

Physician 1 confirmed that the dose delivery device is acceptable for delivery of RT-310 to the prostate and compatible with the use of stepper stabilizer and biplanar ultrasound imaging. His comment about the procedure using the dose delivery device was "that's fine, I like it". He mentioned the procedure would be more difficult without using the dose delivery device as he would have to look at the syringe graduations during the delivery instead of focusing on the ultrasound imaging of the needle position in the prostate, adding risk to the procedure. He also emphasized the importance of the stepper stabilizer to maximize ultrasound probe contact and needle visibility in the sagittal mode. This translates to enhanced delivery location accuracy and precision, being able to use two hands on the delivery device, for improved efficacy and safety.

RT-310 product was mixed and prepared according to the package insert and connected to the 20 G×20 cm Chiba Needle.

Physician 2, a urologist, tested the transperineal implantation of RT-310 using the dose delivery device in a prostate bench model.

Physician 2 positioned the echogenic needle initially under axial view in the prostate model midline then performed transperineal implantation. During delivery the implants exhibited an echogenic appearance potentially due to the precipitated implant (drug and polymer) having a size slightly larger than the needle tract.

Physician 2 confirmed that the dose delivery device is acceptable for delivery of RT-310 to the prostate. His comment about the procedure using the dose delivery device was "Rotation with the thumb was really nice, easy".

Verification Conclusion. The dose delivery device was successfully verified for accuracy and precision and validated to its intended use by physicians in a prostate model. Data demonstrated the dose delivery device enabled delivery of 50 microliter RT-310 implants (or two 25 ul implants) Physicians validated the dose delivery device is acceptable for use for RT-310 delivery via ultrasound imaging and reduces need to view the syringe and maximizes ability to visualize the ultrasound imaging of the needle delivery and as a result reducing risk of implanting RT-310 in the incorrect location and the risk of the procedure.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Clauses

Clause 1. A device comprising a housing; a holder configured to receive a first portion of a needle-syringe; an arm at least partially extending from the housing; wherein the arm includes a surface configured to engage a second portion of the needle-syringe; an actuation member movable with respect to the housing; a worm coupled to the actuation member; a worm gear engaged with the worm; and a pinion gear fixed to the worm gear and engaged with the arm; wherein the arm moves along a translation axis in response to user actuation of the actuation member about a rotational axis.

Clause 2. The device of clause 1, wherein the translation axis is orthogonal to the rotational axis.

Clause 3. The device of any of clauses 1-2, wherein the device is configured to be held by a user hand and the actuation member is configured for actuation by the user hand.

Clause 4. The device of any of clauses 1-3, wherein the actuation member is positioned on a surface of the housing; wherein the surface does not intersect the translation axis.

Clause 5. The device of any of clauses 1-4, wherein the actuation member is a wheel with an indicia providing the user with a tactile or visual indication of the amount of rotation undertaken when the wheel is rotated by the user (e.g., a button, distinguishing color(s), or a dimple).

Clause 6. The device of any of clauses 1-5, wherein the worm is coupled to the actuation member for co-rotation about the rotational axis.

Clause 7. The device of any of clauses 1-6, wherein the pinion gear has a pinion diameter and the worm gear has a worm diameter, wherein the worm diameter is larger than the pinion diameter.

Clause 8. The device of any of clauses 1-7, wherein the pinion gear has gear teeth with a helix angle of 0 degrees.

Clause 9. The device of any of clauses 1-8, wherein the worm gear has gear teeth with a helix angle within a range of 1 degree to 10 degrees.

Clause 10. The device of any of clauses 1-9, wherein the pinion gear is affixed to the worm gear for co-rotation about a gear axis; and wherein the gear axis is orthogonal to the rotational axis of the actuation member and orthogonal to the translation axis of the arm.

Clause 11. The device of any of clauses 1-10, further comprising a gear rack formed on the arm; wherein the pinion gear is enmeshed with the gear rack.

Clause 12. The device of clause 11, wherein the device further defines a one-way transmission comprising the worm, the worm gear, the pinion gear, and the gear rack; or the device further defines a one-way transmission consisting of the worm, the worm gear, the pinion gear, and the gear rack.

Clause 13. The device of clause 12, wherein the one-way transmission has a gear ratio of between 50:1 and 100:1.

Clause 14. The device of any of the preceding clauses, wherein the arm translates 1.27 mm in response to 360 degree rotation of the actuation member.

Clause 15. The device of any of the preceding clauses, wherein the arm moves towards the holder in response to user actuation of the actuation member about the rotational axis.

Clause 16. The device of any of the preceding clauses, wherein the arm moves in a first direction along the translation axis in response to user actuation of the actuation member; and wherein the arm does not move in a second direction opposite the first direction.

Clause 17. The device of any of the preceding clauses, wherein the device further includes a first component comprising the worm and the actuation member; a second component comprising the worm gear and the pinion gear in fixed relationship; and a third component comprising the arm including a gear rack; wherein rotation of the worm causes the worm gear and the pinion gear to rotate at the same rotation rate to thereby causes the surface to extend towards the holder.

Clause 18. A kit comprising: a needle, a syringe; and the device of any of the preceding clauses.

Clause 19. The kit of clause 18, wherein the syringe includes a barrel receivable within the holder, and wherein the syringe includes a plunger that is positioned to engage the surface of the arm when the barrel is received in the holder.

Clause 20. The kit of clause 18, wherein the syringe includes a one-way valve.

Clause 21. The kit of clause 18, further comprising a formulation having a viscosity within a range of 150 centipoise to 300 centipoise, or 100 centerpoise to 500 centerpoise.

Clause 22. The kit of clause 18, further comprising: a cytotoxic or cytostatic drug, solvent and polymer, wherein the cytotoxic or cytostatic drug, solvent and polymer are provided for being combined by a user to form a sustained release formulation (SRF), and wherein the SRF is loaded into the syringe, the needle is attached to the syringe, and the syringe first portion is placed in the holder.

Clause 23. An apparatus comprising: a needle-syringe comprising a plurality of unit volumes of a composition comprising a drug, polymer and solvent; a first portion and a second portion; and a dose delivery device comprising a housing; a holder configured to receive the first portion of the needle-syringe; an arm at least partially extending from the housing; wherein the arm includes a surface configured to engage the second portion of the needle-syringe; an actuation member movable with respect to the housing; a one-way transmission coupled between the actuation member and the arm; wherein the arm moves along a translation axis in response to user actuation of the actuation member about a rotational axis; and wherein the needle-syringe dispenses one of the plurality of unit volumes with a volumetric accuracy of at least 90% in response to the actuation member rotating more than 90 degrees about the rotational axis.

Clause 24. The apparatus of clause 23, wherein the needle-syringe dispenses no more than one of the plurality of unit volumes with an accuracy of at least 90% in response to the actuation member rotating a total rotation within a range of 180 degrees and 720 degrees about the rotational axis.

Clause 25. The apparatus of any of clauses 23-24, wherein the needle-syringe dispenses no more than one of the plurality of unit volumes with an accuracy of at least 90% in response to the actuation member rotating a total rotation within a range of 90 degrees and 360 degrees, or 360 degrees to 720 degrees about the rotational axis.

Clause 26. The apparatus of any of clauses 23-25, wherein each of the plurality of the unit volumes is the same volume and is within a range of 10 μl and 100 μl, 5 μl and 25 μl, or 10 μl and 50 μl.

Clause 27. A method for treating a prostate comprising the steps of: using a needle-syringe coupled to a dose delivery device, the dose delivery device having a user actuation portion, a one-way transmission, and an arm; wherein the arm is configured to engage a plunger of the needle-syringe to dispense no more than a unit volume from the needle; rotating the user actuation portion more than 90 degrees to cause the arm to displace the plunger, thereby dispensing the unit volume from the needle; wherein no more than a unit volume is dispensed from the needle in response to rotating the user actuation portion more than 90 degrees.

Clause 28. The method of clause 27, wherein the unit volume is between 10 μl and 100 μl, or between 25 μl and 50 μl.

Clause 29. The method of any of clause 27-28, wherein the method for treating the prostate treats benign prostatic hyperplasia (BPH).

Clause 30. An apparatus comprising a needle-syringe containing an SRF and a dose delivery device, comprising: a housing; a holder configured to receive a first portion of the needle-syringe; and an arm at least partially extending from the housing. The arm engages a second portion of the needle-syringe. The dose delivery device further comprises an actuation member movable with respect to the housing; a worm coupled to the actuation member; a worm gear engaged with the worm; and a pinion gear fixed to the worm gear and engaged with the arm. The arm moves along a translation axis in response to user actuation of the actuation member about a rotational axis.

Clause 31. The apparatus of clause 30, wherein actuation of the actuation member by between 180 degrees and 720 degrees dispenses 10 μl to 50 μl of the SRF from the syringe-needle.

Clause 32. The apparatus of clause 31, wherein the dose delivery device has a gear ratio of between 50:1 to 100:1 for delivering a unit volume, v, from 10 μl to 50 μl with a greater than 90% accuracy of the delivered unit volume.

Clause 33. The apparatus of clause 32, wherein the SRF has a viscosity of between 100 centipoise and 500 centipoise.

Clause 34. The apparatus of clause 33, wherein the needle-syringe is defined by $$10 < KIR = \frac{\mu L^2}{vD}\left(10^{-6}\right) < 1000$$

where μ is the absolute viscosity (cP) of the composition, L is a needle length (cm) measured from a needle tip to an end of a needle hub, D is a needle lumen diameter (cm), and v is the unit volume of the SFR.

Clause 35. The apparatus of clause 34, wherein the needle-syringe contains at least a plurality of unit volumes, the plurality of unit volumes being a total volume of the SRF for efficacious treatment of BPH.

That which is claimed:

1. A device comprising:

a housing;

a holder configured to receive a first portion of a needle-syringe;

an arm at least partially extending from the housing; wherein the arm includes a surface configured to engage a second portion of the needle-syringe;

an actuation member movable with respect to the housing;

a worm coupled to the actuation member;

a worm gear engaged with the worm; and a pinion gear fixed to the worm gear and engaged with the arm;

wherein the arm moves along a translation axis in response to user actuation of the actuation member about a rotational axis;

wherein the actuation member is positioned on a surface of the housing: wherein the surface of the housing does not intersect the translation axis.

2. The device of claim 1, wherein the translation axis is orthogonal to the rotational axis.

3. The device of claim 1, wherein the device is configured to be held by a user hand and the actuation member is configured for actuation by the user hand.

4. The device of claim 1, wherein the worm is coupled to the actuation member for co-rotation about the rotational axis.

5. The device of claim 1, wherein the pinion gear has a pinion diameter and the worm gear has a worm diameter, wherein the worm diameter is larger than the pinion diameter.

6. The device of claim 1, wherein the pinion gear has gear teeth with a helix angle of 0 degrees.

7. The device of claim 1, wherein the worm gear has gear teeth with a helix angle within a range of 5 degree to 10 degrees.

8. The device of claim 1, wherein the pinion gear is affixed to the worm gear for co-rotation about a gear axis; and wherein the gear axis is orthogonal to the rotational axis of the actuation member and orthogonal to the translation axis of the arm.

9. The device of claim 1, further comprising a gear rack formed on the arm; wherein the pinion gear is enmeshed with the gear rack.

10. The device of claim 9, wherein the device further defines a one-way transmission comprising the worm, the worm gear, the pinion gear, and the gear rack; or the device further defines a one-way transmission consisting of the worm, the worm gear, the pinion gear, and the gear rack.

11. The device of claim 10, wherein the one-way transmission has a gear ratio of between 50:1 and 100:1.

12. The device of claim 1, wherein the device further includes a first component comprising the worm and the actuation member;

a second component comprising the worm gear and the pinion gear in fixed relationship; and a third component comprising the arm including a gear rack;

wherein rotation of the worm causes the worm gear and the pinion gear to rotate at the same rotation rate to thereby cause the surface of the arm to extend towards the holder.

13. An apparatus, comprising:

a needle-syringe containing an SRF, a dose delivery device, comprising:

a housing;

a holder configured to receive a first portion of the needle-syringe;

an arm at least partially extending from the housing; wherein the arm engages a second portion of the needle-syringe;

an actuation member movable with respect to the housing;

a worm coupled to the actuation member;

a worm gear engaged with the worm; and a pinion gear fixed to the worm gear and engaged with the arm;

wherein the arm moves along a translation axis in response to user actuation of the actuation member about a rotational axis, wherein actuation of the actuation member by between 180 degrees and 720 degrees Dispenses 10 μl to 50 μl of the SRF from the needle-syringe.

14. The apparatus of claim 13, wherein the dose delivery device has a gear ratio of between 50:1 to 100:1 for delivering a unit volume, v, from 10 μl to 50 μl with a greater than 90% accuracy of the delivered unit volume.

15. The apparatus of claim 14, wherein the SRF has a viscosity of between 100 centipoise and 500 centipoise.

16. The apparatus of claim 15, wherein the needle-syringe is defined by $$10 < KIR = \frac{\mu L^2}{vD}(10^{-6}) < 1000$$

where μ is the absolute viscosity (cP) of the composition, L is a needle length (cm) measured from a needle tip to an end of a needle hub, D is a needle lumen diameter (cm), and v is the unit volume of the SFR.

17. The apparatus of claim 16, wherein the needle-syringe contains at least a plurality of unit volumes, the plurality of unit volumes being a total volume of the SRF for efficacious treatment of BPH.

18. The apparatus of claim 1, wherein the SRF comprises paclitaxel or docetaxel.

* * * * *